United States Patent
Zilca et al.

(10) Patent No.: US 8,500,635 B2
(45) Date of Patent: Aug. 6, 2013

(54) MOBILE SYSTEM AND METHOD FOR ADDRESSING SYMPTOMS RELATED TO MENTAL HEALTH CONDITIONS

(75) Inventors: Ran Zilca, Briarcliff Manor, NY (US); Robert McGrath, Warwick, NY (US); Sonja Lyubomirsky, Santa Monica, CA (US); Michael Sweeney, New York, NY (US)

(73) Assignee: BLIFE Inc., Santa Clara, CA (US)

( * ) Notice: Subject to any disclaimer, the term of this patent is extended or adjusted under 35 U.S.C. 154(b) by 396 days.

(21) Appl. No.: 12/561,327

(22) Filed: Sep. 17, 2009

(65) Prior Publication Data

US 2011/0066036 A1 Mar. 17, 2011

(51) Int. Cl.
*A61B 5/00* (2006.01)
(52) U.S. Cl.
USPC .......................................... 600/300; 434/236
(58) Field of Classification Search
None
See application file for complete search history.

(56) References Cited

U.S. PATENT DOCUMENTS

| | | | | |
|---|---|---|---|---|
| 5,980,447 | A * | 11/1999 | Trudeau | 600/3 |
| 2003/0179654 | A1* | 9/2003 | Latzke | 368/73 |
| 2008/0208015 | A1* | 8/2008 | Morris et al. | 600/301 |
| 2008/0214903 | A1* | 9/2008 | Orbach | 600/301 |
| 2010/0286490 | A1* | 11/2010 | Koverzin | 600/301 |

* cited by examiner

*Primary Examiner* — Bill Thomson
*Assistant Examiner* — Davin K Sands
(74) *Attorney, Agent, or Firm* — Tutunjian & Bitetto, P.C.

(57) ABSTRACT

A system and method for addressing mental health conditions includes a mobile processing device capable of executing a software application stored in memory. The software application is configured to employ peripheral devices associated with the mobile processing device to provide a user with a self-treating option for addressing mental conditions. When activated, the application provides one more of an interactive diagnosis routine configured to assist in discovering a mental state or condition of the user, and an interactive instructional routine configured to remedy a current mental state.

12 Claims, 3 Drawing Sheets

MOBILE SYSTEM AND METHOD FOR ADDRESSING SYMPTOMS RELATED TO MENTAL HEALTH CONDITIONS

BACKGROUND

1. Technical Field

The present invention relates to human computer interfaces, and more particularly to a mobile system and method employed to treat mental conditions and promote mental health remotely and in real-time.

2. Description of the Related Art

Computer user interfaces permit users to manipulate and use virtual objects that exist in computer software. User interface (UI) devices such as cell phones and personal digital assistants provide interfaces between users and manipulated virtual objects or applications. Many applications (apps) may be provided and employed to support the needs of a user. A need exists for a system and method to promote mental health using mobile devices.

SUMMARY

A system and method for addressing mental health conditions includes a mobile processing device capable of executing a software application stored in memory. The software application is configured to employ peripheral devices associated with the mobile processing device to provide a user with a self-treating option for addressing mental health conditions. When activated, the application provides one more of an interactive diagnosis routine configured to diagnose a mental state or condition of the user, and an interactive instructional routine configured to remedy or alter a current mental state.

A method for addressing mental health conditions includes configuring a software application stored in memory in accordance with a mental health condition of a user; activating the software application to employ peripheral devices associated with the mobile processing device to provide a user with a self-treating option for selectively addressing the mental condition wherein when activated the application provides one more of: an interactive diagnosis routine configured to diagnose a mental state or condition of the user and an interactive instructional routine configured to remedy a current mental state.

Apps in accordance with the present principles can be employed to make the life or daily activities of the user happier (or "more positive") and more fulfilling and to enhance the quality of life of the user.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

Figure 1:
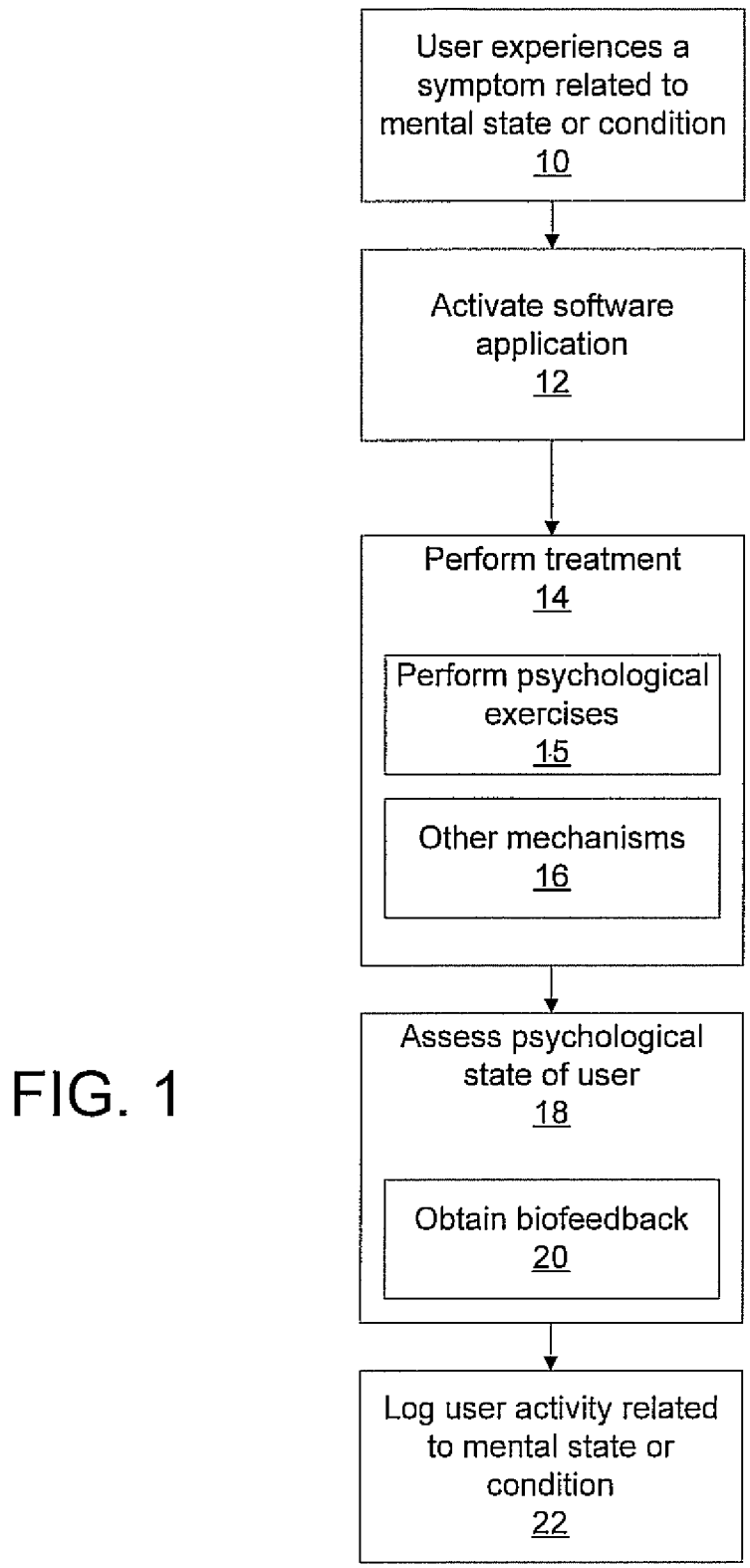
FIG. 1 is a block/flow diagram showing a system/method for addressing mental conditions of a user in accordance with one embodiment.

The present principles are directed to applications for mobile devices. These applications are provided to improve or treat mental health conditions in users. The present principles turn a mobile device into a device for self-treating mental conditions or issues outside the presence of a therapist or healthcare professional. In one embodiment, an application is provided on a mobile device such as a cell phone. The cell phone runs the application in accordance with a user's command when a user feels or experiences a particular mental state. For example, if a particular user has a specific phobia and the user comes in contact with an object or entity related to that phobia, the user may begin to feel anxiety. The user would then open an app on their cell phone configured to provide a treatment routine.

The treatment routine may include one or more interactive exercises to help reduce anxiety and eliminate fears associated with the phobia. For example, cognitive behavioral therapy (or CBT) may be employed. CBT is a psychotherapeutic approach that influences dysfunctional emotions, behaviors and cognitions using goal-oriented, systematic procedures. CBT includes a number of psychological techniques that share a theoretical basis in behavior learning theory and cognitive psychology. Another example of a self-treatment approach may include positive psychology, which studies the strengths and virtues that enable individuals and communities to thrive. Positive psychology seeks to find and nurture positive traits and talent, and make normal life more fulfilling, not simply to treat mental illness.

In other embodiments, the user may simply wish to learn more information about a particular condition. In a particularly useful embodiment, the app is employed to actually help discover or promote provisional diagnose whether the user is suffering from a condition or determine if a user's symptoms are consistent with a condition. If so, the diagnosis may be employed to determine remedial actions in real-time. The user may already know that they are suffering from a condition and may activate an app to assist in remedying the condition. The app may also permit the user access to bibliotherapy (e.g., learning about a condition is known to provide assistance). Bibliotherapy is an expressive therapy that uses an individual's relationship to the content of books and poetry and other written words as therapy. In bibliotherapy, individuals use the content of books, poetry, and other written words as guidance for self-treatment.

Embodiments in accordance with present principles may take the form of an entirely hardware embodiment, an entirely software embodiment or an embodiment including both hardware and software elements. In a preferred embodiment, the present invention is implemented in software, which includes but is not limited to firmware, resident software, microcode, etc.

Furthermore, the present embodiments can take the form of a computer program product accessible from a computer-usable or computer-readable medium providing program code for use by or in connection with a computer or any instruction execution system. For the purposes of this description, a computer-usable or computer readable medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code to reduce the number of times code is retrieved from bulk storage during execution. Input/output or I/O devices (including but not limited to keyboards, displays, pointing devices, etc.) may be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

Referring now to the drawings in which like numerals represent the same or similar elements and initially to FIG. 1, a block/flow diagram depicts a system/method in accordance with one illustrative embodiment. In block 10, a user experiences a symptom or event related to a metal state, condition or disorder, fear or other mental issue. In block 12, a software application is activated that runs on a mobile device and enables the user to do one or more of the following actions.

In block 14, the application performs customized treatment activities. In block 15, interactive psychological exercises (based on clinical psychology methods such as Cognitive Behavior Therapy, Positive Psychology, Bibliotherapy) that alleviate symptoms of mental health conditions such as depression, social anxiety, panic attacks, and general anxiety may be performed.

The exercises may include: ongoing exercises (e.g., positive interventions), one-time modules (e.g., cognitive behavior therapy interactive modules, bibliotherapy reading materials, etc.), and/or immediate action modules designed to treat an immediate difficult state (e.g., small set of instructions to deal with a panic attack). In block 16, other treatment mechanisms may also be employed, such as, e.g., accessing uplifting media (uplifting positive music, audio, photos, video, etc.), playing certain videos or recorded messages, etc.

In block 18, the application may assess the user's psychological state using, e.g., psychological assessment instruments (e.g., depression screening, anxiety screening, positive and negative affect levels, mindfulness level, overall psychological well-being levels) and/or automatic methods based on pattern recognition analysis of data gathered by the mobile device (e.g., location patterns, voice patterns, and other mobile device usage patterns such as use of other applications, use of texting, call to a particular person, etc.). A research method that samples the user's mental state in real-time is called experience sampling. Experience sampling techniques may be employed in determining the state of mind or condition of a user.

In block 20, bio-feedback or any feedback may be obtained to monitor a current state or condition to provide information as to whether improvements have been experienced.

In block 22, the application may include an associated memory and log the events related to the symptoms and/or the treatment. The activity log and assessment results may be shared with a therapist, coach, health professional, or other person and allow the therapist or other person to be involved in the administration of psychological exercises. This can be done in real-time or in a subsequent time-frame.

Figure 2:
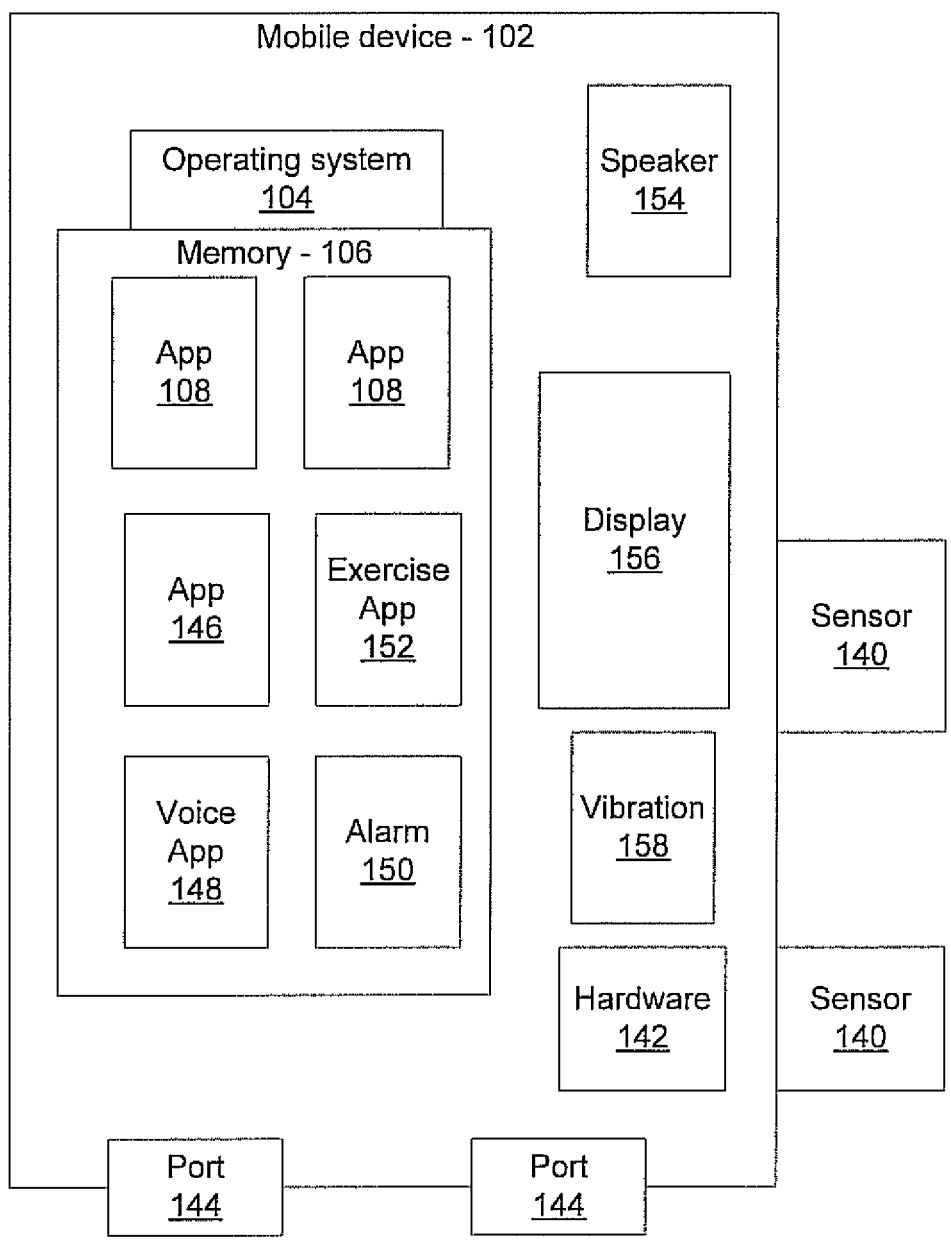
FIG. 2 is a block/flow diagram showing a system for addressing mental conditions of a user in accordance with one embodiment.

Referring to FIG. 2, a system 100 for addressing symptoms of mental health conditions is illustratively shown. System 100 includes a mobile device 102, such as e.g., a cellular telephone, a personal digital assistant, a mobile computer, a specially designed computing device or the like. The device 102 includes an operating system 104 and memory 106 for the storage and execution of one or more applications 108.

In one embodiment, the application 108 includes an "app" for a telephone, such as an APPLE IPHONE® or the like. When a condition or event is experienced by a user that would affect that user's mental state, the user is provided with an opportunity to counter any ill-effects of such a mental state by deploying the app 108.

The following examples are illustrative of some of the functionality provided in accordance with the present principles. In the event that a user experiences a phobia of say, spiders, when the user comes in contact with a spider, the user wants to relieve the anxiety experienced as a result of this event. The user may not have access to a support group, personal aide or health care provider. The user may resort to activating an app associated with this ailment. The app may provide one of several different actions.

In one action, the app provides a soothing voice, music or the like and a reassuring message regarding the phobia. In another action, an instructional video may be played. In yet another application, a procedure may be followed that takes the user or patient through a series of exercises designed to address the symptoms of the phobia. In still other applications, mild obsessive compulsive disorder (OCD) symptoms occur, every time the user has a thought X, the user can activate the app to distract or entertain the user or prompt the user to perform a task, etc.

A healthcare professional may be alerted as a result of the deployment of the app 108 or as a result of direct contact initiated by the user. In another example, cognitive behavior therapy techniques may be employed to change the user's mental state or to help the user cope the situation.

The device 102 may include one or more sensors 140 or feedback gathering hardware 142. Sensors 140 and hardware 142 may include a microphone, heart monitor or electrical contacts for pulse or perspiration monitoring, a device for measuring pupil dilation, a breath monitor, a device to measure perspiration, a device to measure brain activity or waves, a thermometer, etc. Other tools may be provided through attachments to a port or ports 144 located on the device 102. Such tools or medical devices may include a needle for testing blood sugar, a blood pressure device or any other probe of device for taking physical measurements.

Device 102 may include modules or apps 146 designed and configured to produce therapeutic effects. For example, an app 146 may provide a flashing strobe or a color display designed to soothe a patient or user. In another embodiment, an app 146 may be configured to display a puzzle game or other tool employed to distract an individual from anxiety or from having depressed thoughts.

In one embodiment, a voice pattern recognition app 148 may be provided that analyzes a user's speech patterns. This may be employed to analyze a user's telephone conversation as a way of measuring stress levels. The app 148 may compute a score and if the score exceeds a threshold, the app 148 may function as a trigger for app 108. App 148 may also be employed as a step in determining whether a user is in need of therapeutic treatment in accordance with app 108 by asking a user to read a passage, to describe their state of mind, or repeat a rehearsed statement. A comparison may be made with a trained baseline to determine whether a heightened stress level is detected.

Device 102 may include an alarm module 150. The alarm module 150 may employ one or more behavior patterns to determine whether a patient or user is in need of assistance, either using device 102 or by alerting a healthcare professional. In one example, the alarm module 150 monitors a user's location. This may be useful information for obsessive compulsive disorders. Based on a number of times the individual is placed at a particular location of locations, app 108 may be triggered to provide assistance to the user.

Alternatively, a text message, email or phone call may be sent to a friend, family member or healthcare professional where an assessment or determination can be made regarding the user's state or condition. The alarm module 150 may be configured to alert the friend, family member or healthcare professional when any configured condition is met.

App 108 may be configured to include a mental exercise routine module 152. Module 152 may include video, audio, graphical, tactile or any other instructional information. The module 152 may be timed to run automatically, under predetermined measured or input conditions or by direct activation by a user. When activated, the module 152 employs a speaker 154, a display 156, a vibration device 158, etc. to run through an exercise routine with the user. As an example, a daily affirmation program may be provided, a video of a therapist or loved one may be displayed as a pep talk, a 5-step mental exercise method may be run, etc.

The present system provides a self-treatment option for users who may not have access to other forms of treatment. The present system provides helpful tools and exercises that can be performed by an individual without the assistance of others. The present principles provide security and comfort to users at all times and at the user's convenience.

Figure 3:
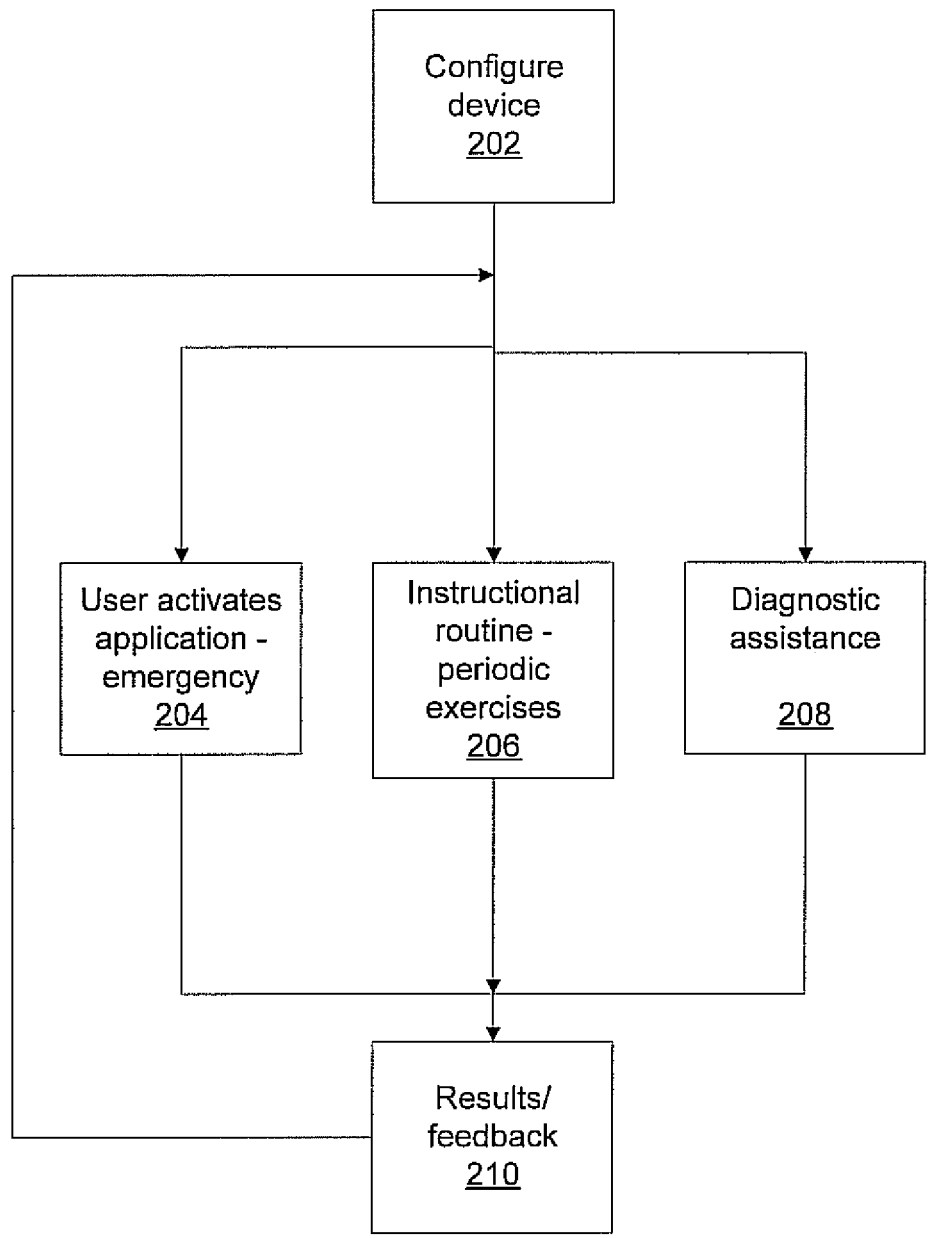
FIG. 3 is a block/flow diagram showing a system/method for addressing mental conditions of a user in accordance with another embodiment.

Referring to FIG. 3, an illustrative example is described to demonstrate a possible implementation of a device with an application for treating or addressing mental conditions or symptoms in accordance with the present principles. In block 202, a user or other person configures a device, such as a telephone or personal digital assistant in accordance with the user's particular condition(s). This may include tailoring the application for the specific user, the specific user's condition and configuring measurement tools (software or hardware). The customization may include programming the device to accommodate the user's specific needs. In addition, different programs or options may be selected from a menu or a previously configured software routine or package.

In block 204, the device is employed as a "panic button." When the user experiences a particular condition or mental state, the user activates the application to assist in dealing with the condition. For example, the individual user suffers from social anxiety and is about to go into a social setting. The activation may have been tailored to run a video of the user's therapist or a general health care provider who offer reassuring words to assist the user. In another example, a user suffers a panic attack. The application provides the user with a step-by-step procedure to control breathing, and to relax the user. Other techniques may include interactive routines using cognitive behavior therapy, etc.

In block 206, the application may be employed as a buddy or instructor in helping the user deal with general issues related to mental health. An example may include daily mental exercises, games directed at building confidence or some other individual characteristic.

In block 208, the application may be employed as a diagnosis tool. The application and the device running the application may be equipped with measurement devices and modules capable of gathering objective (or subjective) data to access the mental state of the user. This may be followed by an alert sent to another individual if certain conditions are experienced. The diagnosis and assessment may employ experience sampling techniques since they measure the state of the user "on the go" in real-time.

In block 210, depending on the results of any branch 204, 206 or 208, any other branch may be activated as part of the overall treatment program. It should be understood that the application may include any one of, a combination of or all of the features described herein. The present principles are particularly useful in situations when the user is alone, or when extra support is needed or desired.

Having described preferred embodiments of a mobile system and method for addressing symptoms related to mental health conditions (which are intended to be illustrative and not limiting), it is noted that modifications and variations can be made by persons skilled in the art in light of the above teachings. It is therefore to be understood that changes may be made in the particular embodiments disclosed which are within the scope and spirit of the invention as outlined by the appended claims. Having thus described aspects of the invention, with the details and particularity required by the patent laws, what is claimed and desired protected by Letters Patent is set forth in the appended claims.

What is claimed is:

1. A system for addressing mental health conditions, comprising:
   a mobile processing device comprising:
      sensors configured to monitor biofeedback from a user in response to the user's input, said sensors including a global positioning system locator and at least one of a microphone, electrical contacts, and an interface port to interface with a medical device, wherein the biofeedback includes one or more of voice patterns, blood pressure, stress level, and heart rate;
      a processor configured to employ peripheral devices associated with the mobile processing device to provide a self-treatment function for addressing mental conditions of the user and further configured to provide an interactive instructional routine to remedy a current mental state, wherein the interactive instructional routine includes a periodic mental exercise routine timed to run automatically to address mental health issues and wherein the interactive instructional routine includes Cognitive Behavior Therapy, Positive Psychology, and Bibliotherapy that uses the user's relationship to the content of written material as guidance for treatment.

2. The system as recited in claim 1, wherein the memory is configured to provide an activity log to store events related to the application.

3. The system as recited in claim 1, wherein the application includes an alarm module configured to notify another person of one of a present mental state of the user and a present activity of the user.

4. The system as recited in claim 1, wherein the mobile processing device includes a mobile telephone.

5. The system as recited in claim 1, further comprising an interactive diagnosis routine configured to assist in discovering a mental state or condition of the user that includes experience sampling techniques.

6. A method for addressing mental health conditions, comprising:
- configuring a software application stored in memory in accordance with a mental health condition of a user;
- monitoring biofeedback from a user in response to the user's input, said biofeedback being measured by sensors that include a global positioning system locator and at least one of a microphone, electrical contacts, and an interface port to interface with a medical device, wherein the biofeedback includes one or more of voice patterns, blood pressure, stress level, and heart rate;
- activating the software application to employ peripheral devices associated with a mobile processing device to provide a self-treatment function for selectively addressing the mental condition of the user, wherein when activated the application provides an interactive instructional routine to remedy a current mental state, wherein the interactive instructional routine includes a periodic mental exercise routine timed to run automatically to address mental health issues and wherein the interactive instructional routine includes Cognitive Behavior Therapy, Positive Psychology, and Bibliotherapy that uses the user's relationship to the content of written material as guidance for treatment.

7. The method as recited in claim 6, further comprising storing an activity log to save events related to the application.

8. The method as recited in claim 6, further comprising notifying another person of one of a present mental state of the user and a present activity of the user by employing an alarm module.

9. The method as recited in claim 6, wherein the mobile processing device includes a mobile telephone.

10. The method as recited in claim 6, further comprising an interactive diagnosis routine configured to assist in discovering a mental state or condition of the user that includes experience sampling techniques.

11. A non-transitory computer readable medium comprising a computer readable application for addressing mental health conditions, wherein the computer readable application when executed on a computer causes the computer to perform the steps of:
- configuring a software application, stored in memory of a mobile processing device, in accordance with a mental health condition of a user;
- monitoring biofeedback from a user in response to the user's input, said biofeedback being measured by sensors that include a global positioning system locator and at least one of a microphone, electrical contacts, and an interface port to interface with a medical device, wherein the biofeedback includes one or more of voice patterns, blood pressure, stress level, and heart rate;
- activating the software application to employ peripheral devices associated with the mobile processing device to provide a self-treatment function for selectively addressing the mental condition of the user, wherein when activated the application provides an interactive instructional routine to remedy a current mental state, wherein the interactive instructional routine includes a periodic mental exercise routing timed to run automatically to address mental health issues and wherein the interactive instructional routine includes Cognitive Behavior Therapy, Positive Psychology, and Bibliotherapy that uses the user's relationship to the content of written material as guidance for treatment.

12. The computer readable medium as recited in claim 11, further comprising an interactive diagnosis routine configured to assist in discovering a mental state or condition of the user that includes experience sampling techniques.

* * * * *